(12) United States Patent
Bernet et al.

(10) Patent No.: US 9,833,068 B2
(45) Date of Patent: Dec. 5, 2017

(54) INSTALLATION OF ANALYTICAL APPARATUS

(71) Applicant: Roche Diagnostics Operations, Inc., Indianapolis, IN (US)

(72) Inventors: Roland Bernet, Immensee (CH); Adri Grefhorst, Ad Varsselder (NL); Bruno Koch, Steinhausen (CH); Franz Lindegger, Sempach (CH); Jeroen Wildenbeest, La Lichtenvoorde (NL)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 132 days.

(21) Appl. No.: 14/475,970

(22) Filed: Sep. 3, 2014

(65) Prior Publication Data

US 2015/0069893 A1 Mar. 12, 2015
US 2015/0351535 A9 Dec. 10, 2015

(30) Foreign Application Priority Data

Sep. 11, 2013 (EP) ..................................... 13183998

(51) Int. Cl.
*A47B 81/00* (2006.01)
*B60B 33/00* (2006.01)
(Continued)

(52) U.S. Cl.
CPC ............ *A47B 81/00* (2013.01); *A47B 91/002* (2013.01); *B60B 33/0002* (2013.01);
(Continued)

(58) Field of Classification Search
CPC ...... A47B 81/00; A47B 91/002; G01N 35/00; G01N 2035/00306; B01L 9/02; B60B 33/0002; B60B 33/00; B62B 3/002
(Continued)

(56) References Cited

U.S. PATENT DOCUMENTS 1,407,690 A * 2/1922 Berry ........................ B62B 1/20
280/47.12
2,935,331 A * 5/1960 Ledgerwood ........... B62B 3/001
280/47.16
(Continued)

FOREIGN PATENT DOCUMENTS

JP 08-044130 A 2/1996

*Primary Examiner* — Daniel J Troy
*Assistant Examiner* — Hiwot Tefera
(74) *Attorney, Agent, or Firm* — Roche Diagnostics Operations, Inc.

(57) ABSTRACT

An analytical apparatus to be installed on a substantially horizontal surface of a diagnostic laboratory is presented. The apparatus comprises a bottom side and an upper working side, the bottom side having at least three casters for rolling the apparatus on a surface and at least two feet. The casters have a fixed height and at least one caster is higher than the other casters so that the apparatus is unbalanced when it is rolled on the surface. The at least two feet are individually adjustable in height so that when the height of the feet is adjusted the upper working side is leveled and the apparatus rests on the at least two feet and the higher caster. An analytical system comprising the analytical apparatus and a method of installing the analytical apparatus and the system are also described.

13 Claims, 4 Drawing Sheets

(51) Int. Cl.
*A47B 91/00* (2006.01)
*G01N 35/00* (2006.01)
*B01L 9/02* (2006.01)

(52) U.S. Cl.
CPC .............. *G01N 35/00* (2013.01); *B01L 9/02* (2013.01); *B60B 33/00* (2013.01); *G01N 2035/00306* (2013.01); *Y10T 29/49826* (2015.01)

(58) Field of Classification Search
USPC ......... 280/47.12, 47.16, 43.24, 79.11, 47.19; 312/249.8, 351.11, 198–203, 298; 108/177
See application file for complete search history.

(56) References Cited

U.S. PATENT DOCUMENTS

| | | | | |
|---|---|---|---|---|
| 3,399,904 A * | 9/1968 | Schinke | ............ | A63C 17/0033 280/47.16 |
| 3,618,966 A * | 11/1971 | Vandervest | ............ | B60B 33/06 280/43.17 |
| 3,685,851 A * | 8/1972 | Berry | ............ | A47B 91/002 280/43.17 |
| 4,102,556 A * | 7/1978 | Webb | ............ | A47B 91/16 16/42 T |
| 4,178,006 A * | 12/1979 | Johnson | ............ | B60B 33/00 280/79.11 |
| 4,433,881 A * | 2/1984 | Witten | ............ | H05K 5/0021 312/107 |
| 4,488,733 A * | 12/1984 | Hellsten | ............ | B62B 3/009 280/47.16 |
| 4,555,827 A * | 12/1985 | St. Louis | ............ | B60B 33/06 16/33 |
| 4,557,534 A * | 12/1985 | Dahnert | ............ | A47B 53/02 312/198 |
| 4,861,049 A * | 8/1989 | Losi | ............ | G07F 19/205 180/275 |
| 5,048,902 A * | 9/1991 | Daly | ............ | B62B 3/006 312/249.8 |
| 5,072,999 A * | 12/1991 | Trotta | ............ | G07C 13/02 235/51 |
| 5,085,447 A * | 2/1992 | Audibert | ............ | A47B 85/00 108/162 |
| 5,113,546 A * | 5/1992 | Parent | ............ | B25H 3/00 15/315 |
| 5,371,922 A * | 12/1994 | Chern | ............ | A47D 13/04 16/35 R |
| 5,556,118 A * | 9/1996 | Kern | ............ | B62B 3/00 280/47.16 |
| 5,810,459 A | 9/1998 | Barrett et al. | | |
| 5,899,467 A * | 5/1999 | Henkel | ............ | A45C 5/14 190/1 |
| 6,095,533 A | 8/2000 | Balolia | | |
| 6,264,219 B1 * | 7/2001 | Smith | ............ | B62B 5/0006 135/125 |
| 6,337,050 B1 | 1/2002 | Takahashi et al. | | |
| 6,443,542 B1 * | 9/2002 | Lindquist | ............ | A47B 87/008 312/111 |
| 6,695,325 B2 * | 2/2004 | Carrillo | ............ | B62B 3/008 280/47.16 |
| 6,824,231 B2 * | 11/2004 | Jakob-Bamberg | ..... | A47B 88/42 211/162 |
| 6,945,615 B1 * | 9/2005 | Cain | ............ | B25H 3/04 312/249.8 |
| 7,044,867 B2 * | 5/2006 | van Nimwegen | ... | A63B 63/083 280/46 |
| 7,281,774 B2 * | 10/2007 | Zenda | ............ | A47B 88/41 312/334.15 |
| 7,527,274 B2 * | 5/2009 | Strauss | ............ | B65G 49/062 211/41.14 |
| 7,747,209 B2 * | 6/2010 | Yamazaki | ............ | G03G 21/1619 312/110 |
| 8,914,925 B2 * | 12/2014 | Angott | ............ | A61B 5/702 128/845 |
| 2002/0043776 A1 | 4/2002 | Chuang | | |
| 2002/0079660 A1 * | 6/2002 | Shirai | ............ | B62B 3/184 280/79.11 |

\* cited by examiner

INSTALLATION OF ANALYTICAL APPARATUS

CROSS-REFERENCE TO RELATED APPLICATIONS

This application is a continuation of EP 13183998.7, filed Sep. 11, 2013, which is hereby incorporated by reference.

BACKGROUND

The present disclosure generally relates to an analytical apparatus to be installed on a surface of a diagnostic laboratory, to an analytical system comprising the analytical apparatus and to a method of installing the analytical apparatus and system.

Analytical apparatuses are typically complex instruments with several operational moving parts. In order to ensure proper functioning, the apparatus has to be leveled. This is even more important with more complex systems comprising a plurality of analytical apparatuses and/or additional modules coupled to each other, where often one or more operational parts are shared between them. It is, for example, possible that a sample is transported from one apparatus or module to another apparatus or module along a transportation unit, e.g. a transportation band, or that a robotic arm is translated along a guiderail back and forth between two or more apparatuses or modules. It is thus important that each apparatus is equally leveled so that there is operational continuity between parts.

Given that the surfaces on which such apparatuses and systems are installed are in general not exactly planar, a mechanism is required for proper positioning and leveling.

For apparatuses of a certain size and weight, which enable manual installation without particular handling tools, it is desirable to have such a positioning and leveling mechanism directly integrated into the apparatus, in order to minimize the number of parts to be mounted and the installation time.

The use of feet attached to the bottom of an apparatus and having an adjustable height is known in the art. The use of casters for easily transporting and moving the apparatus is also known. The combination of adjustable feet and casters is known.

There is a need for a combination and configuration of feet with adjustable height and casters, which has several advantages over the prior art.

SUMMARY

According to the present disclosure, an analytical apparatus to be installed on a substantially horizontal surface of a diagnostic laboratory is presented. The analytical apparatus can comprise an upper working side and a bottom side having attached thereto at least three casters for rolling the apparatus on a surface and at least two feet. The at least three casters can have a fixed height and at least one caster can be higher than the other casters so that the apparatus may be unbalanced when it is rolled on the surface. The at least two feet can be individually adjustable in height so that when the height of the feet is adjusted, the upper working side can be leveled and the apparatus can rest on the at least two feet and the higher caster.

Accordingly, it is a feature of the embodiments of the present disclosure to provide for a combination and configuration of feet with adjustable height and casters. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

Figure 1:
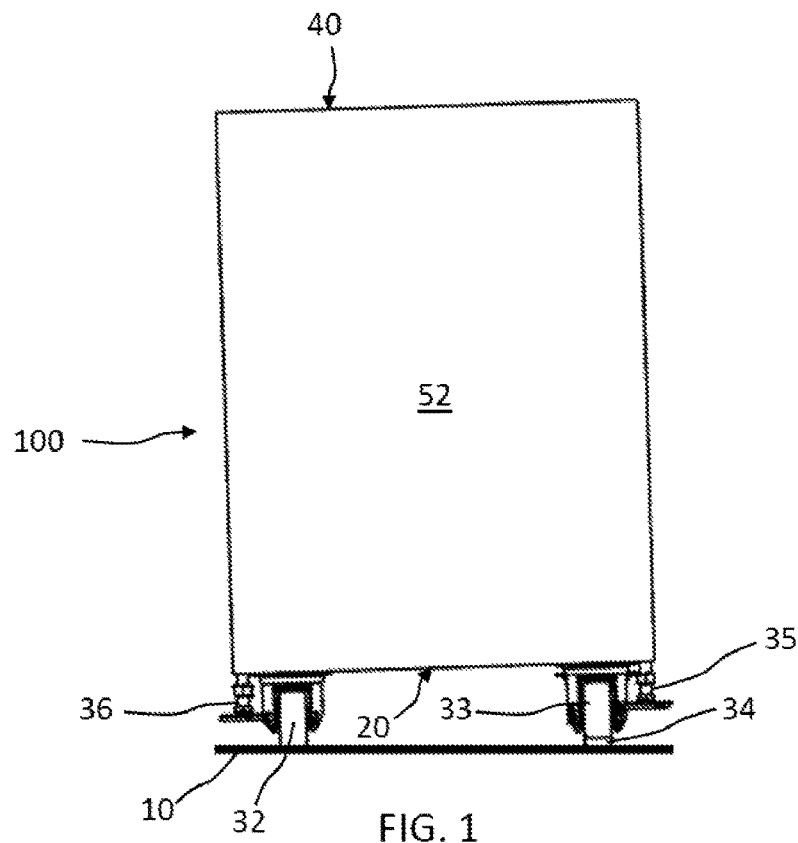
FIG. 1 illustrates schematically a front view of an analytical apparatus before installation according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

An "analytical apparatus" can be a laboratory automated instrument dedicated to the analysis of samples for in vitro diagnostics. Examples of such analytical apparatuses can be clinical chemistry analyzers, coagulation analyzers, immunochemistry analyzers, hematology analyzers, urine analyzers, nucleic acid analyzers, used for the qualitative and/or quantitative detection of analytes present in the samples, to detect the result of chemical or biological reactions or to monitor the progress of chemical or biological reactions. The analytical apparatus can comprise functional units for pipetting and/or mixing of samples and/or reagents. The pipetting unit may comprise a reusable washable needle, for example, a steel needle, or be configured to use disposable pipette tips. The analytical apparatus may comprise a reagent holding unit for holding reagents to perform the analysis. Reagents may be arranged for example in the form of containers or cassettes containing individual reagents or group of reagents, placed in appropriate receptacles or positions within a storage compartment or conveyor. It may comprise a consumable feeding unit, for example, for feeding reaction vessels. The analytical apparatus can further comprise one or more mixing units, comprising, for example, a shaker to shake a cuvette or vessel comprising a liquid or a mixing paddle to mix liquids in a cuvette or reagent container. The analytical apparatus can further comprise a particular detection system and follow a particular workflow, for example, execute a number of processing steps, which are optimized for certain types of analysis.

The analytical apparatus may have different configurations according to the need and/or according to the desired laboratory workflow. Additional configurations may be obtained by coupling a plurality of apparatuses together and/or adding modules. The term "module" can herein be used to indicate a work cell, typically smaller in size and weight than the analytical apparatus, which can have an auxiliary function to the analytical function of an analytical apparatus and can work only together with an analytical apparatus. In particular, a module can cooperate with one or more analytical apparatuses for carrying out dedicated tasks of a sample processing workflow, which can occur for example before or after analysis of the sample, e.g. by performing one or more pre-analytical and/or post-analytical steps. Examples of the pre-analytical and/or post-analytical steps can be loading and/or unloading and/or transporting and/or storing sample tubes or racks comprising sample tubes, loading and/or unloading and/or transporting and/or storing reagent containers or cassettes, loading and/or unloading and/or transporting and/or storing and/or washing reagent vessels such as, for example, cuvettes, loading and/or unloading and/or transporting and/or storing pipette tips or tip racks, reading and/or writing information bearing codes, for example, barcodes or RFID tags, washing pipette tips or needles or reaction vessels, for example, cuvettes, mixing paddles, mixing of samples with other liquid, e.g. reagents, solvents, diluents, buffers, decapping, recapping, pipetting, aliquoting, centrifuging, and the like. An example of such a module can be a sample loading and/or unloading unit for loading/unloading sample tubes.

The term "coupling" or "coupled" can refer either to the coupling of two analytical apparatuses or to the coupling of at least one analytical apparatus to at least one module in a manner that functional cooperation and/or synergies, for example, by sharing of functional units, are enabled.

The term "sample" can refer to a material suspected of containing an analyte of interest. The sample can be derived from any biological source, such as a physiological fluid, including, blood, saliva, ocular lens fluid, cerebral spinal fluid, sweat, urine, milk, ascites fluid, mucous, synovial fluid, peritoneal fluid, amniotic fluid, tissue, cells or the like. The test sample can be pretreated prior to use, such as preparing plasma from blood, diluting viscous fluids, lysis or the like; methods of treatment can involve filtration, distillation, concentration, inactivation of interfering components, and the addition of reagents. A sample may be used directly as obtained from the source or following a pretreatment to modify the character of the sample, e.g. after being diluted with another solution or after having being mixed with reagents e.g. to carry out one or more diagnostic analyses like e.g. clinical chemistry assays, immunoassays, coagulation assays, nucleic acid testing, and the like. The term "sample" can therefore not be only used for the original sample but can also relate to a sample which has already been processed (pipetted, diluted, mixed with reagents, enriched, having been purified, having been centrifuged, etc.). As used herein, the term "analyte" can refer to a compound or composition to be detected or measured, i.e. analyzed.

Analytical apparatuses and modules can generally comprise an upper working side including a mount platform, frame or structure, where most of the functional units can form an automated workstation. The upper working side can be closed with a cover and can be made accessible from the outside at least in part by opening the cover. The cover can be at least partially transparent in order to follow the operation of the functional units on the upper working side.

The analytical apparatus described herein can comprise a bottom side having attached thereto at least three casters for rolling the apparatus on a surface. The term "caster" can refer to a wheel that can be mounted to the bottom of an object, in this case the bottom side of an analytical apparatus or module, so as to enable that object to be easily moved, e.g. by pulling and/or pushing the object, so that the object can roll on a surface. Any type of caster known in the art can in principle be used as long as it can sustain the weight of the object. A caster can be rigid, basically comprising a wheel mounted to a stationary fork. The orientation of the fork, which can be fixed relative to the object, can determine when the caster can be mounted to the bottom side. Rigid casters tend to restrict motion so that the object can travel along a straight line. Swivel casters incorporate a wheel mounted to a fork, but an additional swivel joint above the fork can allow the fork to freely rotate about 360°, thus enabling the wheel to roll in any direction. This can make it possible to easily move the object in any direction without changing its orientation. Alternatively, spherical wheels, generally comprising a spherical ball mounted inside a restraining fixture, can be used. Common inexpensive casters may include a brake, which can prevent the wheel from turning. This can be commonly achieved using a lever that presses a brake cam against the wheel. According to an embodiment, at least one of the casters can be a swivel caster or of the ball type. According to an embodiment, at least one of the casters can include a brake.

The casters of the analytical apparatus can have a fixed height, meaning that the distance from the bottom of the wheel to the bottom side of the analytical apparatus can remain constant for each caster individually. However, this distance can be longer for one the casters than for the other casters, i.e. one of the casters can be higher than the other casters. This caster can be referred to as the "higher caster". According to certain embodiments, the higher caster can be about 5 mm (millimeters) to about 15 mm higher than the other casters. According to an embodiment, the higher caster can be about 10 mm higher than the other casters. This height difference between the casters can result in an unbalanced rolling of the analytical apparatus on a substantially flat horizontal surface. In other words, the distance of the bottom side of the analytical apparatus from the surface can be larger at the point where the higher caster is mounted and smaller where the other casters are mounted, resulting in a slight tilt of the apparatus. Also, in case more than three casters are mounted, e.g. four casters, the analytical apparatus can normally rest on only three casters at a time in contact with the surface, one of which can be the higher caster. This unbalanced arrangement can be acceptable for short distances, e.g. for a few meters, e.g. when moving the analytical apparatus from a transportation pallet to an installation position on the surface of a laboratory.

The analytical apparatus can further comprise at least two adjustable feet attached to the bottom side. The term "foot" or "feet" can refer to a rigid elevation element on which the analytical apparatus can rest when installed on a surface and capable of maintaining the bottom side elevated with respect to the surface. The term "adjustable" can relate to the capability of the feet to be adjusted upwards or downwards independently of each other. Thus, each foot can be individually adjustable in height so that when the height of the feet is adjusted, the upper working side can be leveled and the apparatus can rest on the at least two feet and the higher caster. The adjustable height range can be, for example, of a few millimeters or of a few centimeters, for example, about plus/minus approximately 1 centimeter or more, so that the total height of each foot can be about the height of the higher caster plus/minus the adjustable height range when the analytical apparatus is installed on a surface.

Any type of adjustable feet known in the art can in principle be used as long as they can sustain the weight of the object resting on them. One of the simplest forms of adjustable foot can comprise a spindle and threaded nut mechanism, where height adjustment can be achieved by screwing the nut relative to the spindle.

The term "surface" as used herein can relate to an area at least as large as the footprint of the analytical apparatus, on which the analytical apparatus is to be installed, and which can be substantially horizontal. The surface may include a floor of a laboratory or a platform placed on or above the floor, including a table top or a fixture hanging from a wall or from a ceiling. The term "substantially horizontal" can refer to nearly flat and planar appearance, which may however be uneven, can comprise, for example, recesses, bulging parts or inclinations, not necessarily visible by eye.

The term "installed" or "installation" can refer to an even leveled position of the analytical apparatus at a desired location, which can enable the apparatus to function according to the specifications and expectations. The term "installing" thus can include positioning, i.e. placing an analytical apparatus at a desired location on a surface, for example, by rolling, and leveling the apparatus by adjusting the height of the feet such as to compensate for eventual unevenness of the surface.

The apparatus may comprise one more integrated levels, for example, circular levels, e.g. on the upper working side to facilitate the leveling process. For example, one or more circular levels may be located at particular positions of the upper working side where leveling is most important.

According to certain embodiments, the bottom side can be substantially rectangular and can comprise a rear edge, a front edge adjacent to an accessible front side and opposite to the rear edge, and two lateral edges. According to an embodiment, the higher caster can be located at a corner between the rear edge and a lateral edge, a first foot can be located at a corner between the front edge and the same lateral edge, and a second foot can be located at an intermediate position of the other lateral edge. This arrangement can allow comfortable access to both adjustable feet for height adjustment even when the analytical apparatus is installed at a corner of a room with the rear edge and a lateral edge both close to a respective wall, where "close" can mean that the distance can be small enough for a person not to be able to walk between the analytical apparatus and the wall, but possibly large enough for an arm to reach the second foot. Alternatively, the second foot may be located at a distance from the front edge, which can be reachable with an arm and/or, for example, a screwing tool from the bottom side.

According to certain embodiments, the analytical apparatus can have a weight below about 500 Kg.

According to certain embodiments, the analytical apparatus can have a footprint of less than about 1 square meter ($m^2$).

Analytical apparatuses in this weight and footprint range can be more easily handed during transportation and installation and can be installed on most surfaces of analytical laboratories, which can normally stand such a load per square meter.

According to some embodiments, the analytical apparatus can comprise at least one side comprising fastening elements for hanging a module having an upper working side such that when the upper working side of the analytical apparatus is leveled, the upper working side of the module can also be leveled. The fastening elements may otherwise be configured for coupling two analytical apparatuses side by side.

An analytical system is also disclosed. According to certain embodiments, the system can comprise an analytical apparatus and a module coupled to the analytical apparatus such as to hang from one side of the analytical apparatus with its upper working side equally leveled with the upper working side of the analytical apparatus.

According to some embodiments, the system can comprise a plurality of analytical apparatuses coupled directly to each other side by side or via at least one intermediate module wherein the upper working sides of the respective apparatuses/modules can be equally leveled.

A method of installing an apparatus on a substantially horizontal surface of a diagnostic laboratory is herein also described. The method can comprise rolling the apparatus on at least three casters, one of which being higher than the other casters, to a desired installation position on the surface and adjusting the height of the at least two feet until the upper working side is leveled and the apparatus can rest on the at least two feet and the higher caster.

Thus, the height of the adjustable feet can be at the beginning shorter than the height of the casters so that when the analytical apparatus is rolled, they do not contact the surface. Once the apparatus has reached the desired installation position, the height of the adjustable feet can be increased as necessary until the apparatus is leveled. At the end of this operation, the apparatus can rest on the adjustable feet and on the higher caster, while contact between the surface and the other casters is normally lost.

The method may further comprise coupling a module to the apparatus, where coupling the module to the apparatus can comprise rolling the module and/or the apparatus until the module and the apparatus are positioned next to each other, lifting and attaching the module to a side of the apparatus so that the module can hang from the apparatus.

Thus, a module may also comprise casters, for example, 4 casters, e.g. having the same height, for rolling the module to a desired position. Once the analytical apparatus is installed, contact between the module and the surface can normally be lost as the module hangs from the analytical apparatus and can remain suspended above the surface. Alternatively, a module may comprise a bottom side similar to that of an analytical apparatus and be configured to be installed analogously to an analytical apparatus.

According to some embodiments, the method can comprise coupling a plurality of apparatuses directly to each other or via at least one intermediate module. The method can comprise adjusting the height of the at least two feet of each apparatus until the upper working sides of the respective apparatuses/modules are equally leveled.

A method of re-installing an apparatus on a substantially horizontal surface of a diagnostic laboratory is also described. The method can comprise de-installing an apparatus previously installed. De-installing can comprise adjusting the height of the at least two feet so that the apparatus can rest on the at least three casters and optionally rolling the apparatus out of the installation position. The method can further comprise repeating any of the above described installation steps. For example, an analytical apparatus may be de-installed in order to facilitate service or for relocation to another installation position. Also, an original configuration may be changed at a later stage by, for example, coupling one or more modules and/or one or more analytical apparatuses. In such cases, it may be advantageous to first de-install the previously installed analytical apparatus or system, possibly including rolling the apparatus out of the installation position, to attach then one or more analytical apparatuses and/or modules according to the desired new configuration, to move then all together to the original installation position or to a new position and to repeat the installation procedure by adjusting the feet. Even in case the previously installed analytical apparatus or system is not moved before attaching other modules and/or other analytical apparatuses, it may be advantageous to de-install the previously installed analytical apparatus so that the installation procedure can be repeated ex-novo in order to take into account the newly added parts and ensure that equal leveling for all can be achieved.

There are many advantages of the proposed system. One advantage can be that the complexity of the mechanism can be minimized. The mechanism can also be inexpensive and compact. Another advantage can be that the installation time can be reduced. Another advantage can be that it can enable easy installation regardless of space availability. For example, installation can be made possible in small rooms with limited space for maneuverability or difficult accessibility. Also space can be gained, by making it possible to install the apparatus, for example, close to the walls at the corner of a room. For the same reason, serviceability can also be improved. This can be achieved with a minimum of two feet having adjustable height and three casters having a fixed height attached to the bottom side of the apparatus.

Figure 2:
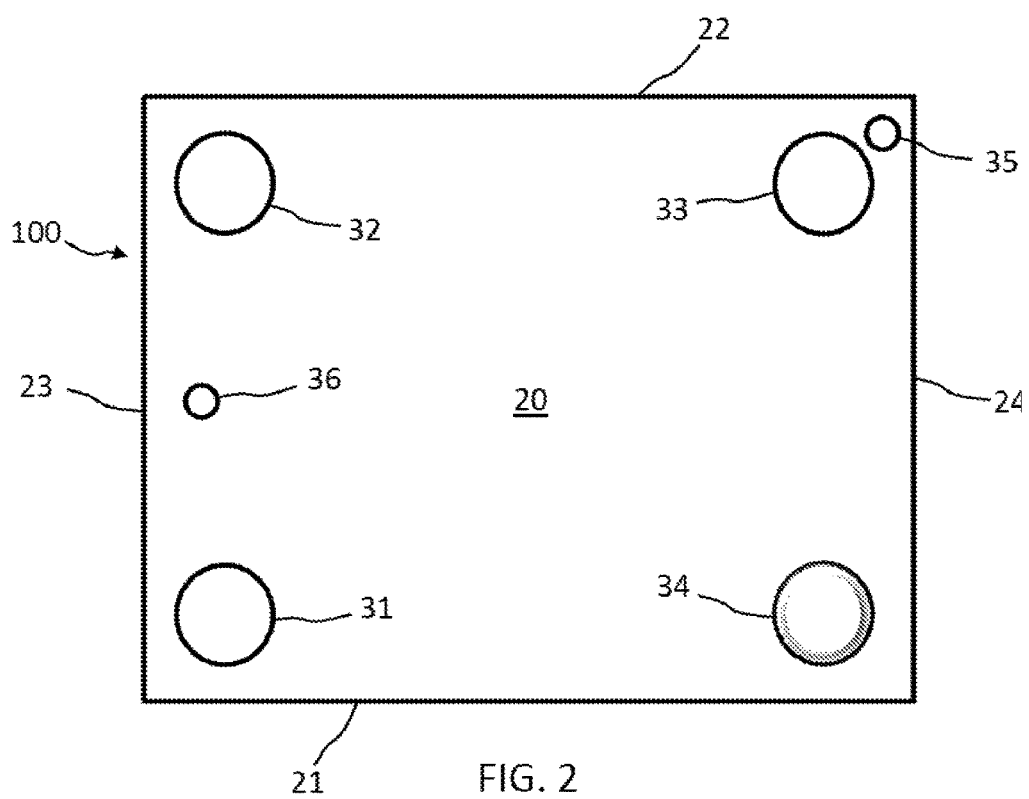
FIG. 2 illustrates schematically the bottom side of the analytical apparatus of FIG. 1 according to an embodiment of the present disclosure.

Referring initially to FIG. 1 and FIG. 2, FIG. 1 and FIG. 2 show schematically a front view and a bottom view respectively of an analytical apparatus 100 to be installed on a substantially horizontal surface 10 of a diagnostic laboratory. The apparatus 100 can comprise a bottom side 20, an upper working side 40 and a front side 52 from which the upper work side can be accessible. The bottom side 20 can be substantially rectangular and can comprise a rear edge 21, a front edge 22 adjacent to the front side 52 and opposite to the rear edge 21, and two lateral edges 23, 24 forming four corners.

The bottom side 20 can also comprise four casters 31, 32, 33, 34, attached to respective corners of the bottom side 20, for rolling the apparatus 100 on the surface 10. The casters 31, 32, 33, 34 can have a fixed height and, in one embodiment, casters 31, 32, 33 can have the same height, whereas caster 34 can be about 10 mm higher than the other casters 31, 32, 33. Caster 34 can be referred to as the higher caster and, in this example, can be located at a corner between the rear edge 21 and a lateral edge 24. This arrangement can result in an unbalanced, tilted condition of the analytical apparatus 100, as shown in FIG. 1, with only three casters at a time being in contact with the surface 10, one of which being the higher caster 34. Which of the other three casters 31, 32, 33, is out of contact with the surface at a given time can depend on the barycenter of the analytical apparatus 100 and/or on the direction of the force applied when handling the analytical apparatus 100. In FIG. 1, caster 33 is shown as an example out of contact with the surface 10 and the apparatus 100 is slightly tilted towards the casters 31, 32.

The apparatus 100 can further comprise two feet 35, 36, attached to the bottom side 20. One foot 35 can be attached at the corner between the front edge 22 and the lateral edge 24 next to caster 33. The other foot 36 can be located at an intermediate position of the other lateral edge 23 between casters 31, 32. The feet 35, 36 can be individually adjustable in height and are shown in a retracted position in FIG. 1 with a height shorter than the height of the casters 31, 32, 33, 34, such as to be out of contact with the surface 10 and allow free rolling of the apparatus 100 on the casters 31, 32, 33, 34.

Figure 3:
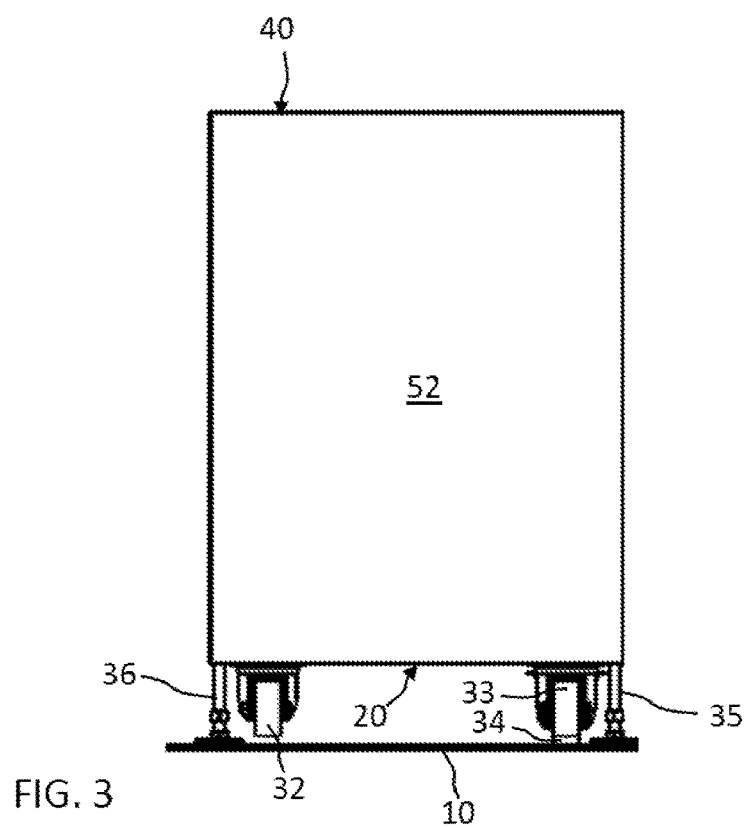
FIG. 3 illustrates schematically the same front view of the analytical apparatus of FIG. 1 after installation according to an embodiment of the present disclosure.

FIG. 3 shows schematically the same front view of the analytical apparatus 100 of FIG. 1 after installation. For installing the analytical apparatus 100 on the surface 10, the apparatus 100 can be rolled on the casters 31, 32, 33, 34 to a desired installation position on the surface 10. The height of the feet 35, 36 can then be adjusted so that they are now higher than the casters 31, 32, 33 and the apparatus rests only the two feet 35, 36 and the higher caster 34 in contact with the surface 10, while the casters 31, 32, 33, have lost contact with the surface 10. More in particular, the height of the feet 35, 36 can be individually adjusted so that the upper working side 40 is leveled.

Figure 4:
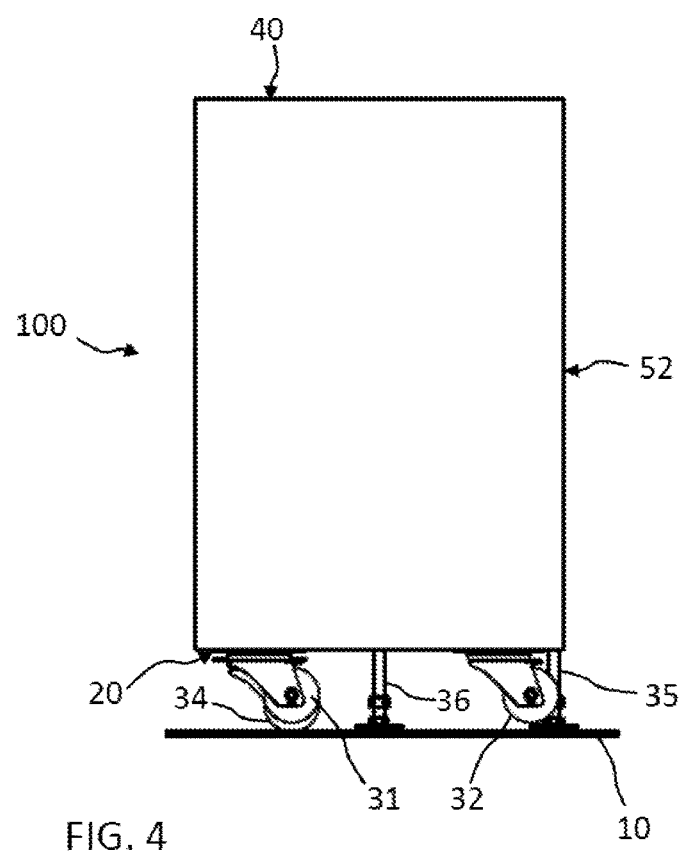
FIG. 4 illustrates schematically a side view of the same analytical apparatus of FIG. 3 after installation according to an embodiment of the present disclosure.

FIG. 4 shows schematically a side view of the same installed analytical apparatus 100 of FIG. 3.

The apparatus 100 can have a weight below about 500 Kg and a footprint less than about 1 m², thereby occupying an area of the surface 10, which can be less than about 1 m².

Figure 5:
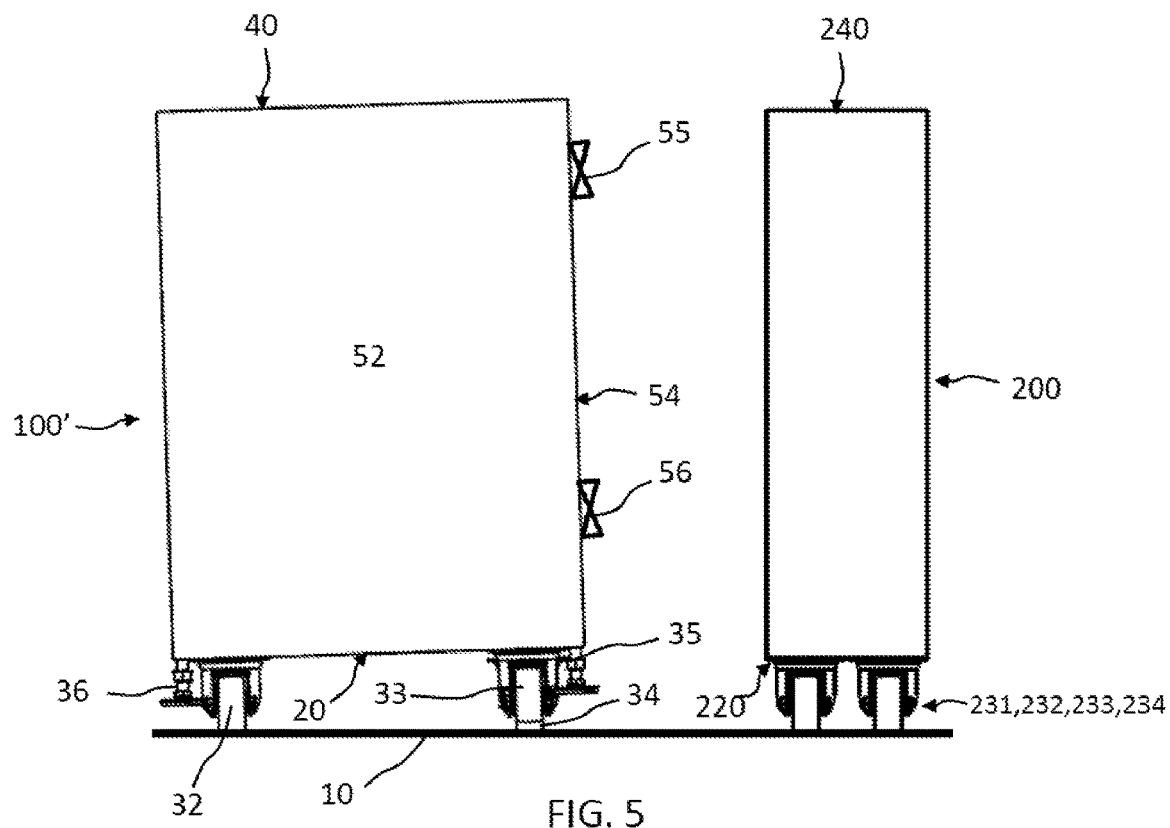
FIG. 5 illustrates schematically an analytical apparatus and a module to be coupled to the analytical apparatus according to an embodiment of the present disclosure.

FIG. 5 shows schematically an analytical apparatus 100' and a module 200 to be coupled to the analytical apparatus 100'. The analytical apparatus 100' can be the same as the analytical apparatus 100 of FIG. 1, with the exception that it can further comprise fastening elements 55, 56 on one side 54 for coupling with the module 200. The module 200 can have an upper working side 240 and a bottom side 220. The bottom side 220 can comprise four casters 231, 232, 233, 234, all having the same height, for rolling on a surface 10. The module 200 can be shorter than the analytical apparatus 100'.

Coupling the module 200 to the apparatus 100' can comprise rolling the module 200 and/or the apparatus 100' until the module 200 and the apparatus 100' are positioned next to each other, lifting and attaching the module 200 to the side 54 of the apparatus using the fastening elements 54, 55 so that the upper working surface 40 of the analytical apparatus 100' and the upper working surface 240 of the module 200 can be aligned with each other.

Given that the module 200 is shorter than the analytical apparatus 100', the module 200 can remain at an elevated position hanging from the side 54 of the apparatus 100' and with the casters 231, 232, 233, 234 out of contact with the surface 10. The apparatus 100' and the module 200 attached to the apparatus 100' can then be rolled on the casters 31, 32, 33, 34 of the apparatus 100' to a desired installation position on the surface 10 if different from the current position. As already described above with respect to FIG. 3, the height of the feet 35, 36 can then be individually adjusted so that the upper working side 40 can be leveled. By leveling the upper working side 40 of the apparatus 100', the upper working side 240 of the module 200 can thereby also be leveled.

Figure 6:
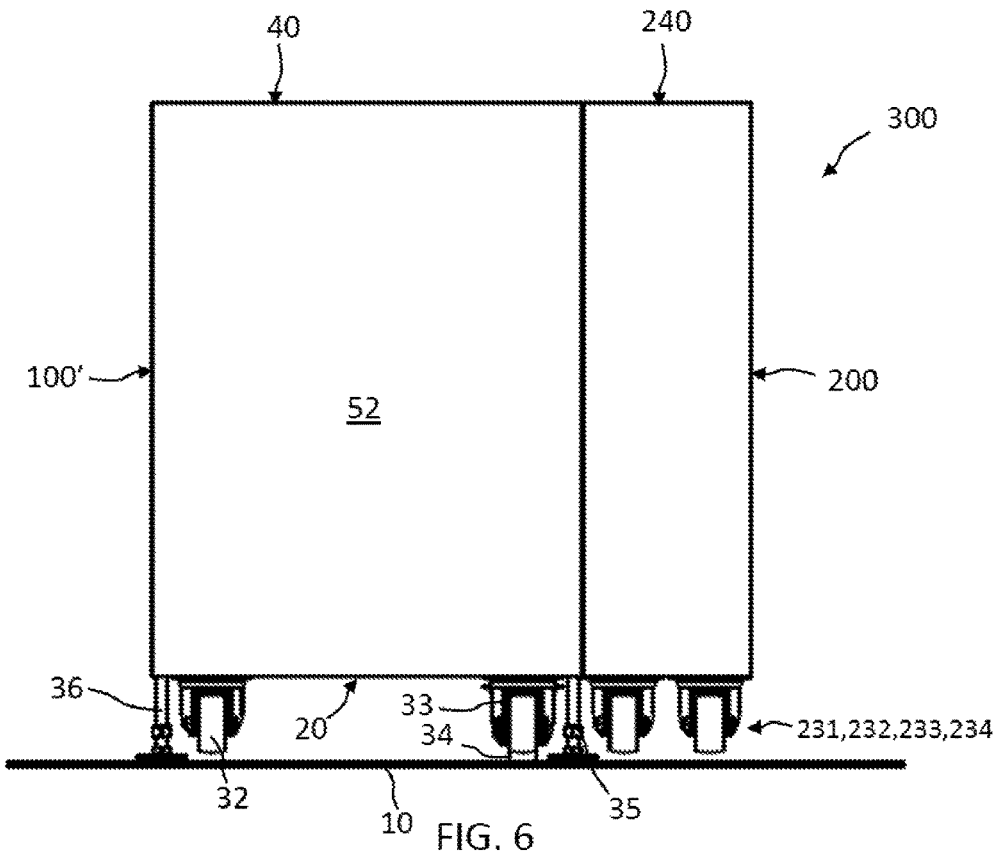
FIG. 6 illustrates schematically an installed analytical system comprising the analytical apparatus and the module of FIG. 5 coupled to each other according to an embodiment of the present disclosure.

FIG. 6 shows schematically an installed analytical system 300 comprising the analytical apparatus 100' and the module 200 of FIG. 5 resulting from this coupling and installation operation.

Figure 7:
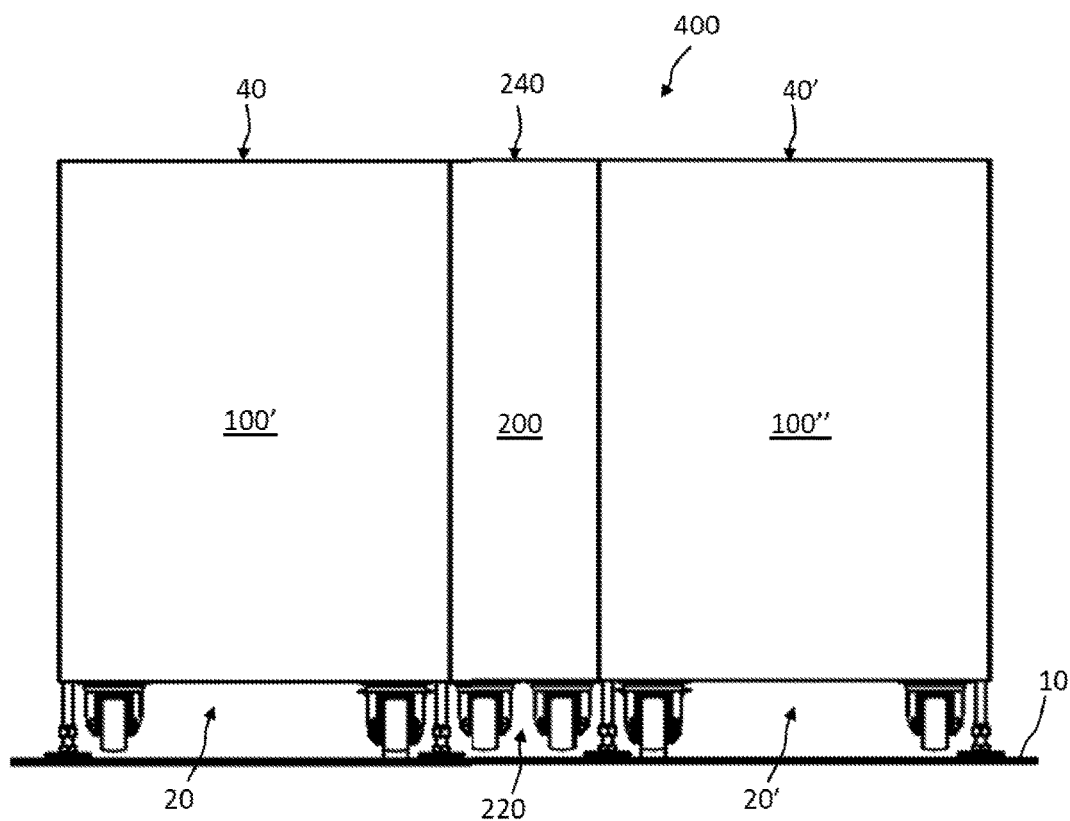
FIG. 7 illustrates an installed analytical system comprising two analytical apparatuses coupled to an intermediate module according to an embodiment of the present disclosure.

FIG. 7 shows an analytical system 400 comprising two analytical apparatuses 100', 100'' coupled via an intermediate module 200 and installed in a similar manner. The analytical apparatus 100' and the module 200 can be the same as those in FIG. 6. The analytical apparatus 100" can be similar to the analytical apparatus 100' and can comprise an upper working side 40' and a bottom side 20'. The bottom side 20' can be the same as the bottom side 20 of the analytical apparatus 100, 100' of FIGS. 1 to 6, except that it can be mirrored. Installing the analytical system 400 can comprise, in this case, adjusting the height of the feet 35, 36 of each apparatus 100', 100" until the upper working sides 40, 40', 240 of the respective apparatuses 100', 100" and of the module 200 are equally leveled. As can be seen from FIG. 7, the module 200 can be out of contact with the surface 10, hanging between the apparatus 100' and the apparatus 100" in an elevated position above the surface 10. According to an embodiment, the analytical apparatuses 100', 100" can be coupled directly to each other.

Installing the analytical systems 300, 400 may comprise de-installing an analytical apparatus 100' or analytical system 300 previously installed by adjusting the height of the feet 35, 36 so that the apparatus 100' can rest on at least three of the casters 31, 32, 33, 34, including caster 34 and optionally rolling the apparatus 100' or system 300 out of the installation position. The method can further comprise coupling the module 200 to the apparatus 100' or the apparatus 100" to the system 300 and repeating the installation as above described.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

For the purposes of describing and defining the present disclosure, it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

We claim:

1. An analytical apparatus to be installed on a substantially horizontal surface of a diagnostic laboratory, the analytical apparatus comprising:
    an upper working side; and
    a bottom side having attached thereto at least three casters for rolling the apparatus on a surface and at least two feet, wherein the at least three casters have a fixed height and one caster is higher than the other casters so that the apparatus is unbalanced when it is rolled on the surface, wherein the at least two feet are individually adjustable in height so that when the height of the feet is adjusted, the upper working side is leveled and the apparatus rests independently on only the at least two feet and the higher caster, wherein the bottom side is rectangular and comprises a rear edge, a front edge opposite to the rear edge, and two lateral edges, and wherein the higher caster is located at a corner between the rear edge and a lateral edge, one of the at least two feet is located at a corner between the front edge and the same lateral edge, and the other of the at least two feet is located at an intermediate position of the other lateral edge.

2. The apparatus according to claim 1, wherein the higher caster is 10 mm higher than the other casters.

3. The apparatus according to claim 1, wherein the apparatus has a weight below 500 Kg.

4. The apparatus according to claim 1, wherein the apparatus has a footprint of less than 1 m$^2$.

5. The apparatus according to claim 1, further comprising fastening elements for coupling another apparatus or a module having an upper working side such that when the upper working side of the apparatus is leveled, the upper working side of the module is also leveled.

6. An analytical system comprising an analytical apparatus according to claim 5 and a module coupled to the analytical apparatus.

7. An analytical system comprising a plurality of apparatuses according to claim 1 coupled directly to each other or via at least one intermediate module wherein the upper working sides of the respective apparatuses are equally leveled.

8. A method of installing an apparatus according to claim 1 on a substantially horizontal surface of a diagnostic laboratory, the method comprising:
    rolling the apparatus on at least three casters to a desired installation position on the surface; and
    adjusting the height of the at least two feet until the upper working side is leveled and the apparatus rests on the at least two feet and the higher caster.

9. The method according to claim 8, further comprising, coupling a module to the apparatus.

10. The method according to claim 9, wherein coupling the module to the apparatus comprises,
    rolling the module and/or the apparatus until the module and the apparatus are positioned next to each other, and
    attaching the module to a side of the apparatus so that the module hangs from the apparatus.

11. The method according to claim 8, further comprising, coupling a plurality of apparatuses directly to each other or via at least one intermediate module.

12. The method according to claim 11, further comprising, adjusting the height of the at least two feet of each apparatus until the upper working sides of the plurality of apparatuses is equally leveled.

13. A method of re-installing an apparatus on a substantially horizontal surface of a diagnostic laboratory, the method comprising:
    de-installing an apparatus previously installed according to the method of claim 8, wherein de-installing comprises adjusting the height of the at least two feet so that the apparatus rests on the at least three casters and optionally rolling the apparatus out of the installation position; and
    repeating any of the steps of claim 8.

* * * * *